United States Patent
Yonezawa

(10) Patent No.: US 6,556,291 B2
(45) Date of Patent: Apr. 29, 2003

(54) DEFECT INSPECTION METHOD AND DEFECT INSPECTION APPARATUS

(75) Inventor: Eiji Yonezawa, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/867,600

(22) Filed: May 31, 2001

(65) Prior Publication Data
US 2001/0048522 A1 Dec. 6, 2001

(30) Foreign Application Priority Data
May 31, 2000 (JP) ........................... 2000-166497

(51) Int. Cl.⁷ ................................ G01N 21/00
(52) U.S. Cl. .................... 356/237.2; 356/73; 356/237.1
(58) Field of Search .................... 356/237.1, 237.2, 356/237.3, 237.4, 237.5, 600, 601, 73; 382/141, 144, 145, 149, 225; 395/11, 21–23

(56) References Cited

U.S. PATENT DOCUMENTS

| 5,003,615 A | | 3/1991 | Seitz | |
|---|---|---|---|---|
| 5,479,575 A | * | 12/1995 | Yoda | 356/32 |
| 5,544,256 A | * | 8/1996 | Brecher et al. | 382/149 |
| 5,572,598 A | | 11/1996 | Wihl et al. | |
| 5,737,072 A | * | 4/1998 | Emery et al. | 382/237.2 |
| 5,768,476 A | * | 6/1998 | Sugaya et al. | 395/21 |
| 5,812,259 A | | 9/1998 | Yoshino et al. | |
| 5,828,500 A | | 10/1998 | Kida et al. | |
| 5,847,822 A | | 12/1998 | Sugiura et al. | |
| 5,880,838 A | | 3/1999 | Marx et al. | |
| 5,889,593 A | | 3/1999 | Bareket | |
| 6,122,397 A | * | 9/2000 | Lee et al. | 382/149 |
| 6,148,097 A | | 11/2000 | Nakayama et al. | |
| 6,222,624 B1 | | 4/2001 | Yonezawa | 356/237.1 |

FOREIGN PATENT DOCUMENTS

| EP | 0 426 166 | * | 10/1990 | |
|---|---|---|---|---|
| EP | 0 563 897 A1 | | 3/1993 | G01N/21/89 |
| EP | 0 628 806 A2 | | 12/1994 | |
| EP | 0 977 029 A1 | | 2/2000 | G01N/21/88 |
| JP | 6-76069 | | 3/1994 | G06F/15/70 |
| JP | 6-235625 | | 8/1994 | G01B/11/30 |
| JP | 07 027 709 | * | 1/1995 | |
| JP | 09-209710 | | 8/1997 | |
| JP | 10 144 747 | * | 5/1998 | |
| JP | 10 282 011 | * | 10/1998 | |

* cited by examiner

Primary Examiner—Frank G. Font
Assistant Examiner—Sang H. Nguyen
(74) Attorney, Agent, or Firm—Sughrue Mion, PLLC

(57) ABSTRACT

A defect inspection apparatus for inspecting a presence of a defect on an object includes: a first input unit which inputs wavelength characteristics of each of a plurality of samples with wavelength variation of an illumination light for inspection; a second input unit which inputs inspection conditions which an inspector sets for each of the samples as a teaching signal; a third input unit which inputs a wavelength characteristic of the object with the wavelength variation of the illumination light; a neural network which learns and stores a relationship between the inputted wavelength characteristic of each sample and the inputted inspection condition for each sample, and determines an inspection condition for the object based on the inputted wavelength characteristic of the object and the learned relationship; and a defect detector which detects a defect of the object based on the determined inspection condition of the object.

12 Claims, 4 Drawing Sheets

DEFECT INSPECTION METHOD AND DEFECT INSPECTION APPARATUS

BACKGROUND OF THE INVENTION

1. Field of the Invention

The present invention relates to a defect inspection method of inspecting whether an object of inspection has a defect or not and a defect inspection apparatus used for the inspection.

2. Related Art

When the surface of an object such as a semiconductor wafer is to be inspected for a defect, an optimum inspection condition differs depending upon the type of the object of inspection (a workpiece) and a manufacturing process. Heretofore, to achieve such an optimum inspection condition an inspector is required to be individually checked and set for every type of object of inspection and every manufacturing process.

However, in case the types of objects of inspection are very many and new types are successively required to be inspected for a short period, it is cumbersome and inefficient to individually check and further set an optimum inspection condition. Further, even if the automation of such inspection is tried, it is difficult to automate the setting of an inspection condition.

SUMMARY OF THE INVENTION

The invention is made in view of the problems of the related type technique and has a technical object of providing a defect inspection method and a defect inspection apparatus using the method wherein a new type of object of inspection can be efficiently inspected and the automation of inspection is enabled.

To achieve the above object, according to a first aspect of the invention, there is provided a defect inspection method of inspecting a presence of a defect on an object, the defect inspection method including the steps of:

inputting a wavelength characteristic of each of a plurality or samples with wavelength variation of an illumination light for inspection;

inputting an inspection condition which an inspector voluntary sets for each sample as a teaching signal;

learning and storing a relationship between the inputted wavelength characteristic of each sample and the inputted inspection condition for each sample as a learning;

inputting a wavelength characteristic of the object with the wavelength variation of the illumination light;

determining an inspection condition for the object based on the inputted wavelength characteristic of the object and the learning; and detecting a defect of the object based on the determined inspection condition for the object.

According to a second aspect of the invention, the defect inspection method of the first aspect further includes the step of:

learning and storing a relationship between the inputted wavelength characteristic of the object and the determined inspection condition for the object as the learning.

According to a third aspect of the invention, the defect inspection method of the first aspect, in the learning and storing step, the relationship between the wavelength characteristic of the following sample and the inspection condition for the following sample is learned and stored referring to the relationship between the wavelength characteristic of the previous sample and the inspection condition for the previous sample.

According to a fourth aspect of the invention, the defect inspection method of the first aspect, the leaning and storing step is executed by a neural network.

According to a fifth aspect of the invention, the defect inspection method of the first aspect, the defect inspection method includes a method of macroscopically inspecting the presence of the defect on the object having a minute pattern.

According to a sixth aspect of the invention, the defect inspection method of the first aspect further includes the steps of:

illuminating each of the samples and the object while varying a wavelength of the illumination light;

capturing images of each of the samples and the object using reflected lights or transmitted lights of the illumination lights having different wavelengths; and detecting the wavelength characteristic of each of the samples and the object based on the images captured using the illumination lights having different wavelengths.

According to a seventh aspect of the invention, the defect inspection method of the sixth aspect, the wavelength characteristic includes luminance information of the reflected lights or the transmitted lights with the wavelength variation of the illumination light.

According to an eighth aspect of the invention, the defect inspection method of the first aspect, the detecting step includes the steps of:

executing differential processing between a reference image data and an image of the object for obtaining a differential image;

binarizing the differential image for obtaining a binarization data; and detecting a defect based on the binarization data.

According to a ninth aspect of the invention, the defect inspection method of the eighth aspect, the inspection condition includes a threshold level referred in the binarizing step.

According to a tenth aspect of the invention, the defect inspection method of the eighth aspect, the detecting step includes a step of filtering the differential image, the inspection condition includes a parameter for the filtering.

Further to achieve the object, according to an eleventh aspect of the invention, there is provided a defect inspection apparatus for inspecting a presence of a defect on an object, the defect inspection apparatus including:

a first input unit which inputs a wavelength characteristic of each of a plurality of samples with wavelength variation of an illumination light for inspection;

a second input unit which inputs an inspection condition which an inspector voluntary sets for each sample as a teaching signal;

a third input unit which inputs a wavelength characteristic of the object with the wavelength variation of the illumination light;

a learning unit which learns and stores a relationship between the inputted wavelength characteristic of each sample and the inputted inspection condition for each sample as a learning, and determines an inspection condition for the object based on the inputted wavelength characteristic of the object and the learning; and a defect detector which detects a defect of the object based on the determined inspection condition of the object.

According to a twelfth aspect of the invention, the defect inspection method of the eleventh aspect, the learning unit learns and stores a relationship between the inputted wavelength characteristic of the object and the determined inspection condition for the object as the learning.

According to a thirteenth aspect of the invention, the defect inspection method of the eleventh aspect, the learning unit learns and stores the relationship between the wavelength characteristic of the following sample and the inspection condition for the following sample referring to the relationship between the wavelength characteristic of the previous sample and the inspection condition for the previous sample.

According to a fourteenth aspect of the invention, the defect inspection method of the eleventh aspect, the learning unit includes a neural network.

According to a fifteenth aspect of the invention, the defect inspection method of the eleventh aspect, the defect inspection apparatus includes an apparatus for macroscopically inspecting the presence of the defect on the object having a minute pattern.

According to a sixteenth aspect of the invention, the defect inspection method of the eleventh aspect further includes:

an illuminating unit which illuminates each of the samples and the object while varying a wavelength of the illumination light;

an image unit which captures images of each of the samples and the object using reflected lights or transmitted lights of the illumination lights having different wavelengths; and a wavelength characteristic detector which detects the wavelength characteristic of each of the samples and the object based on the images captured using the illumination lights having different wavelengths.

According to a seventeenth aspect of the invention, the defect inspection method of the sixteenth aspect, the wavelength characteristic includes luminance information of the reflected lights or the transmitted lights with the wavelength variation of the illumination light.

According to an eighteenth aspect of the invention, the defect inspection method of the eleventh aspect, the defect detector executes differential processing between a reference image data and an image of the object for obtaining a differential image, binarizes the differential image for obtaining a binarization data, and detects the defect based on the binarization data.

According to a nineteenth aspect of the invention, the defect inspection method of the eighteenth aspect, the inspection condition includes a threshold level referred for binarizing.

According to a twelfth aspect of the invention, the defect inspection method of the eighteenth aspect, the defect detector filters the differential image, the inspection condition includes a parameter for filtering.

DESCRIPTION OF THE PREFERRED EMBODIMENT

Figure 1:
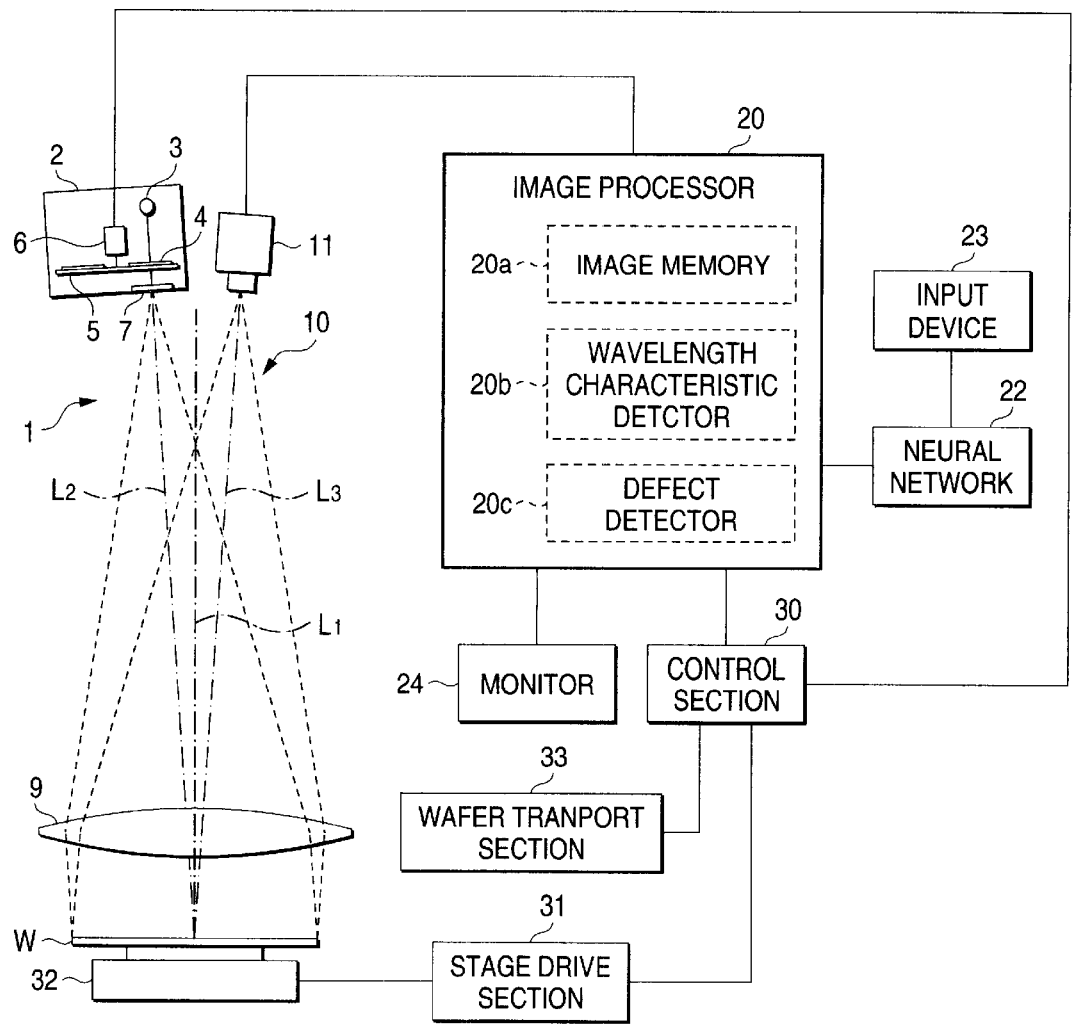
FIG. 1 is a schematic diagram showing an arrangement of an inspection apparatus according to the present invention.

A preferred embodiment of the present invention will be described hereinafter by reference to the accompanying drawings. FIG. 1 is a diagram showing an arrangement of an inspection apparatus according to the present invention.

Reference numeral 1 designates an illumination optical system for illuminating a wafer W which is placed on an XY stage 32 and is to be inspected (i.e., an object). The illumination optical system 1 is equipped with an illumination unit 2 and a collimator lens 9, which is greater in diameter than an inspection surface of the wafer W. Reference numeral 10 designates an image pick-up optical system for capturing (imaging) an image of the wafer W illuminated by the illumination optical system 1. The collimator lens 9 is shared between the illumination optical system 1 and the image pick-up optical system 10, and the image pick-up optical system 10 is equipped with a CCD camera 11.

The optical axis L3 of the image pick-up optical system 10 is arranged symmetrical to the optical axis L2 of the illumination optical system 1 with respect to the optical axis L1 of the collimator lens 9. As a result, the camera 11 can obtain an image of an inspection surface of the wafer W with regular reflection (reflected light) from the wafer W illuminated by the illumination optical system 1. The camera 11 is arranged so as to obtain an image of the wafer W in a direction substantially perpendicular to a surface of the wafer W while avoiding interference with the illumination unit 2. In the present embodiment, each of the angle formed between the optical axes L1 and L2 and the angle formed between the optical axes L1 and L3 is set to be three degrees. Since the inclination of the optical axis L3 relative to the inspection surface of the wafer W is not great, an image is less susceptible to distortion or defocusing.

The optical axis L2 of the illumination optical system 1 may be arranged to be identical to the optical axis L1 of the lens 9 to illuminate the wafer W at a right angle, and the optical axis L3 of the image pick-up optical system 10 may be arranged to be identical to the optical axis L2 of the illumination optical system 1. In this case, using of a half mirror, the image pick-up optical system 10 obtains an image of the inspection surface of the wafer W with the regular reflection from the inspection surface while avoiding interference between the illumination unit 2 and the camera 11.

The illumination unit 2 comprises a halogen lamp 3 serving as a light source; a rotary plate 5 having a plurality of wavelength selection filters 4 and an opening for white illumination; a motor 6 for rotating the rotary plate 5; and a diffusion plate 7. The filters 4 selectively convert white illumination light emitted from the lamp 3 into narrow-band lights having respective center wavelengths. The plurality of filters 4 are provided so as to switch over the center wavelengths of narrow-band lights at predetermined intervals. In the present embodiment, to obtain sixteen images of different wavelengths for one sheet of the wafer, the filters 4 are so designed as to convert white illumination light selectively into narrow-band lights of sixteen types, the center wavelengths of which are distributed at predetermined intervals and fall within a range of 450 nm to 850 nm.

The rotary plate 5 is rotated by the motor 6, and a desired filter 4 or an opening is selectively disposed on an optical path of the illumination light. The light that has passed through the filter 4 or the opening is diffused by the diffusion plate 7, thereby producing diffused illumination light having sufficiently uniform brightness. The thus-diffused light is substantially collimated by the lens 9 to the parallel illumination light, which illuminates the wafer W placed on the stage 32.

The regular reflection from the wafer W illuminated by illumination light is converged by the lens 9, so that an image of substantially the entire surface of the wafer W is formed on the camera 11 having the image pick-up element.

The rotary plate 5 having the filters 4, etc. may be provided in the image pick-up optical system 10 side (i.e., in front of the camera 11). Further, the wavelength of white illumination light may be changed using a monochromator instead of the wavelength selection filters 4.

In the case of an object of inspection that transmits light, the object of inspection is imaged by the transmitted light using a camera 11.

Image data from the camera 11 is input to an image processor 20. The image processor 20 is provided with an image memory 20a storing image data, a wavelength characteristic detector 20b which detects the wavelength characteristic (the characteristic of one wafer with the variation of the wavelength of illumination light) of the wafer from the plural image data different in a wavelength of one wafer stored in the memory 20a, and a defect detector 20c that detects the defect of a resist pattern and others applied to the wafer.

Figure 2:
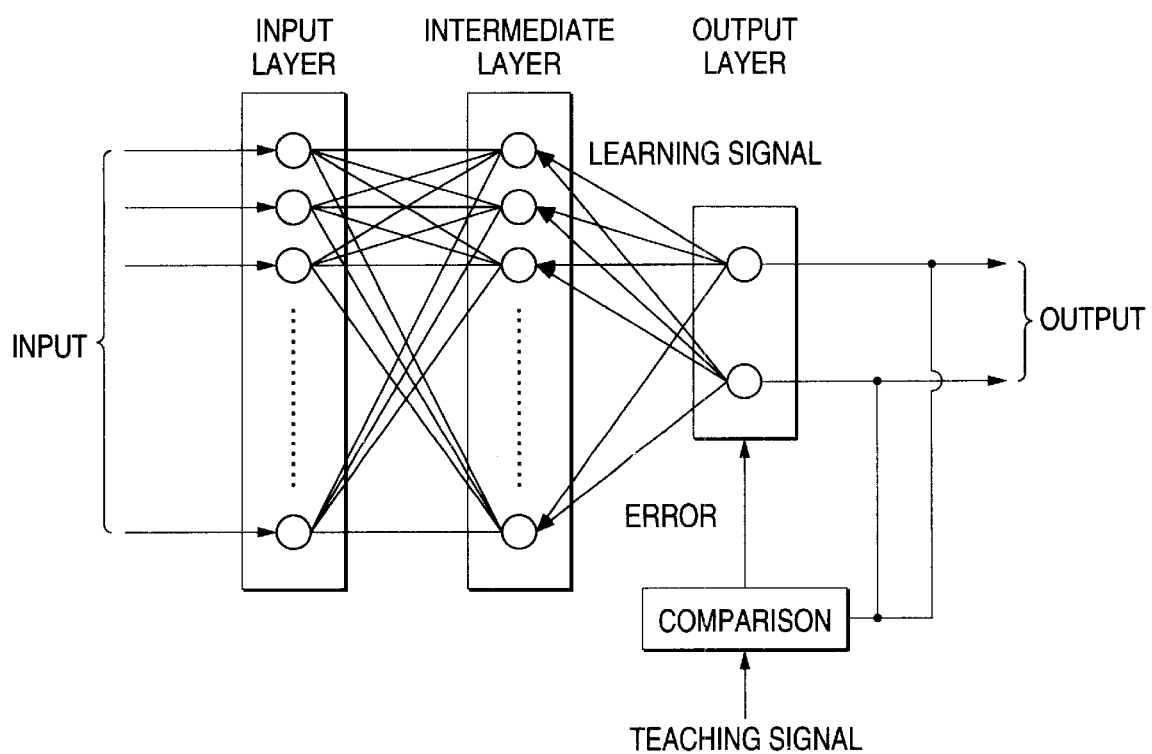
FIG. 2 is an explanatory drawing for explaining a neural network.

Reference numeral 22 designates a neural network. The neural network 22 is composed of an input layer, one or plural intermediate layers and an output layer as shown in FIG. 2. Learning in the neural network 22 will be described later in detail as an example using generally known back-propagation.

Reference numeral 31 designates a stage drive section for moving the stage 32, and reference numeral 33 designates a wafer transport section for automatically moving a wafer W to the stage 32. Reference numeral 30 designates a control section for controlling the entire defect inspection apparatus.

Figure 4:
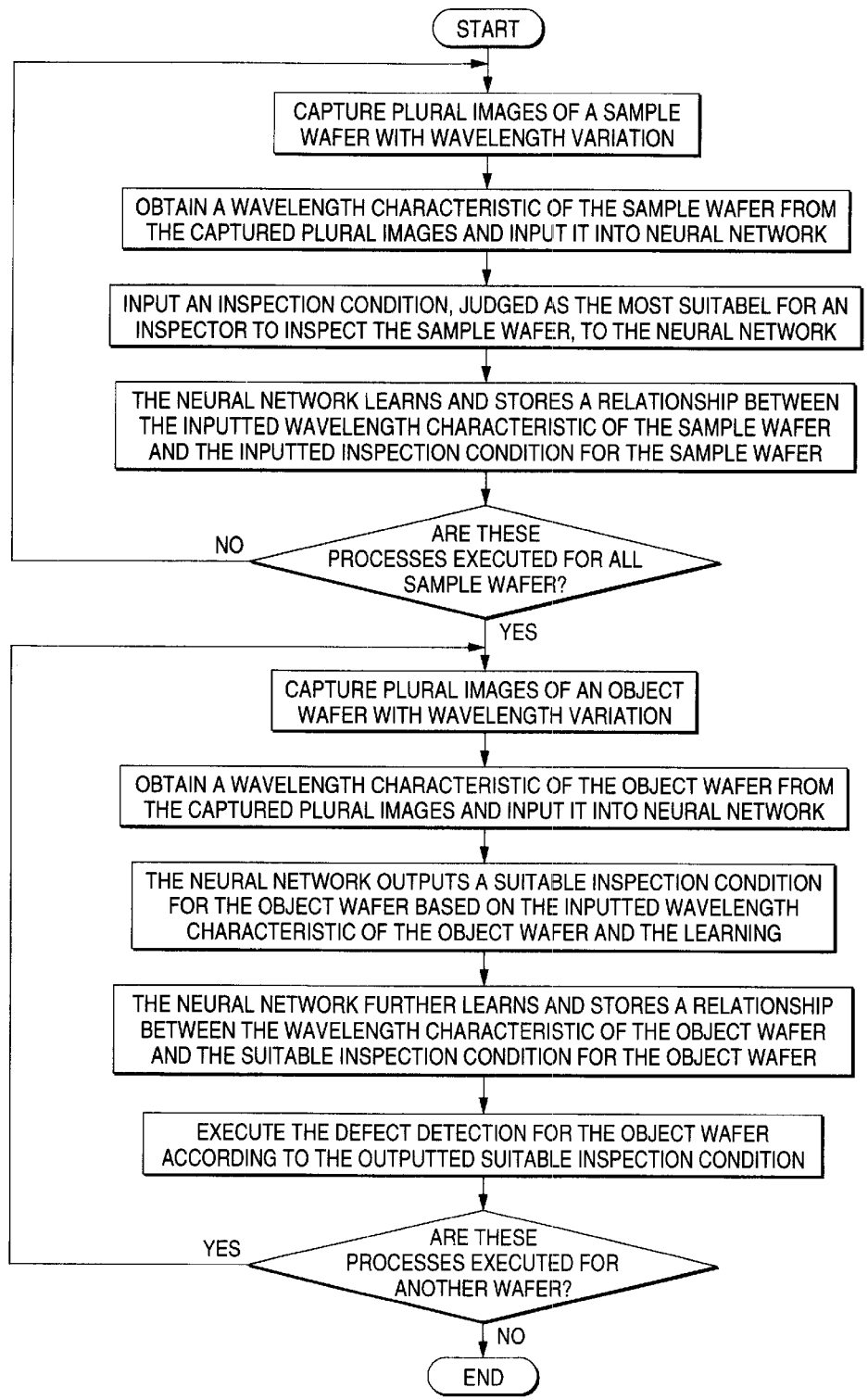
FIG. 4 is a flowchart for explaining learning (storage) and the output of an optimum inspection condition respectively by the neural network.

Next, the defect inspection by this apparatus will be described. In case of macroscopically inspecting whether a semiconductor wafer has a defect or not, an inspection condition varies in accordance with the type and the manufacturing process of a wafer due to difference in the thickness of a resist formed over the wafer and the substrate thereof. It is difficult to theoretically analyze these because these show a complex interference characteristic, however, it is certain that a detected wavelength characteristic includes the information of the thickness of a resist and its substrate. Therefore, the neural network 22 is caused to learn the relationship between each wavelength characteristic and each inspection condition of plural (multiple) wafers and store it, and when the wavelength characteristic of a new wafer is acquired (input), the optimum inspection condition of the wafer is output based upon the storage (learning). An unknown wafer (an object of inspection) can be sufficiently practically inspected by performing defect inspection using an inspection condition output from the neural network 22 as described above, and labor for setting an inspection condition can be greatly reduced. Learning (storage) and the output of an optimum inspection condition in the neural network 22 will be described below (refer to a flowchart shown in FIG. 4).

First, multiple sample wafers whose the inspection condition is determined for every type are prepared. One of the samples is put on the stage 32 and is imaged while varying the wavelength of light illuminated by the illumination unit 2. The motor 6 is driven under the control of the controller 30 and the 16 types of filters 4 in the path of illumination light is changed, so that the wavelength of illumination light for illuminating the wafer W is selectively changed. Sixteen image data of one wafer W imaged by the camera 11 by synchronizing with the variation of the wavelength of illumination light under the control of the controller 30 are sequentially stored in the memory 20a.

Figure 3:
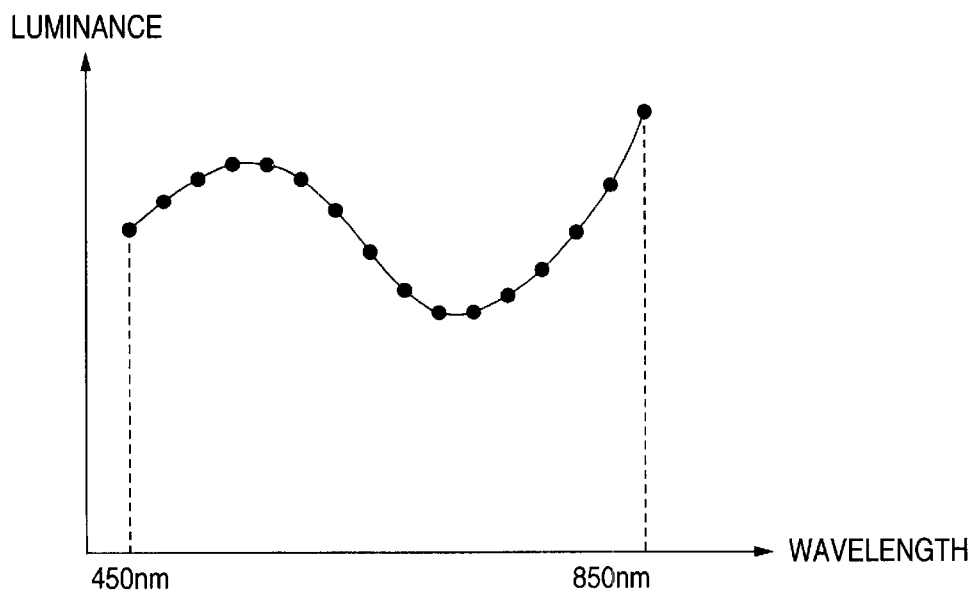
FIG. 3 shows an example in which the luminance information of an image of a sample wafer with wavelength variation is plotted.

Next, the detector 20b obtains the wavelength characteristic based on each image data stored in the memory 20a. The wavelength characteristic obtained by the detector 20b is input to the neural network 22. FIG. 3 shows an example in which the luminance information of the image of the sample wafer with wavelength variation is plotted; the x-axis shows a wavelength and the y-axis shows luminance information. Average luminance and local luminance in each wavelength can be input to the neural network 22 as they are as a wavelength characteristic, however, the following data calculated based upon these information may be also input. For example, for the following data described above, the average value, the maximum value, the minimum value, difference between the maximum value and the minimum value (variation width) of a set of the average luminance for each wavelength, a inclination of a straight line which is obtained by approximating a wavelength-luminance curve with least squares method, the residual sum of squares (the total value of the square of difference) of the straight line, the periodicity of luminance variation, etc can be also given.

Further, an inspection condition (checked by an inspector beforehand, that is, an inspection condition judged as the most suitable for an inspector to inspect a sample wafer) corresponding to the wavelength characteristic of the sample wafer is input from an input device 23 to the neural network 22 as a teaching signal. A condition for defect inspection in a wafer manufacturing process is as follows.

In case that the inspection, for checking whether a resist pattern is precisely formed in the wafer manufacturing process by utilizing the macro image of a wafer, is performed, a defect is generally detected by executing differential processing between a reference imagen and the image of an object of inspection. For the detection of a defect, the binarization of whether the value of each pixel in a differential image is larger than a set value (a threshold level) or not is executed, the presence of the defect is judged if the value is larger than the set value. The threshold level for binarization is equivalent to an inspection condition.

Also, when the differential image is processed through a band-pass filer before the binarization, a specific frequency component is detected. When the passing band (a parameter) of the band-pass filer is changed, another defect can be emphasized. A parameter of filtering processing in such image processing may be also used for an inspection condition. In case the detection sensitivity of a defect is high at a specific wavelength, an illuminating condition on which the wavelength is acquired may be also used for an inspection condition.

The wavelength characteristic and the inspection condition of all sample wafers the inspection condition of which is already determined are input to the neural network 22. When a new wavelength characteristic is input from the detector 20b to the neural network 22 and further, an inspection condition corresponding to the new wavelength characteristic is input from the input device 23 as a teaching signal, relationship between the wavelength characteristic and the inspection condition is learned and stored referring to already learned (stored) contents. That is, learning (storage) is performed so that an inspection condition corresponding to the following wavelength characteristic is output in case a certain wavelength characteristic is input.

When the learning of the sample wafer whose the inspection condition is determined is finished as described above, plural images of a new unknown type of wafer W whose the inspection condition is not determined are imaged while varying the wavelength of illumination light and are input to the image processor 20. The detector 20b obtains the wavelength characteristic (the above-mentioned item of the wavelength characteristic) based on each image data stored in the memory 20a and inputs it to the neural network 22. The neural network 22 outputs an optimum inspection condition (that is, a threshold level for binarization in image processing, a parameter of filtering processing for emphasizing a defect or an illuminating condition and others) of the new wafer W based upon learning (storage) up to then. The output is input to the detector 20c.

Figure 5:
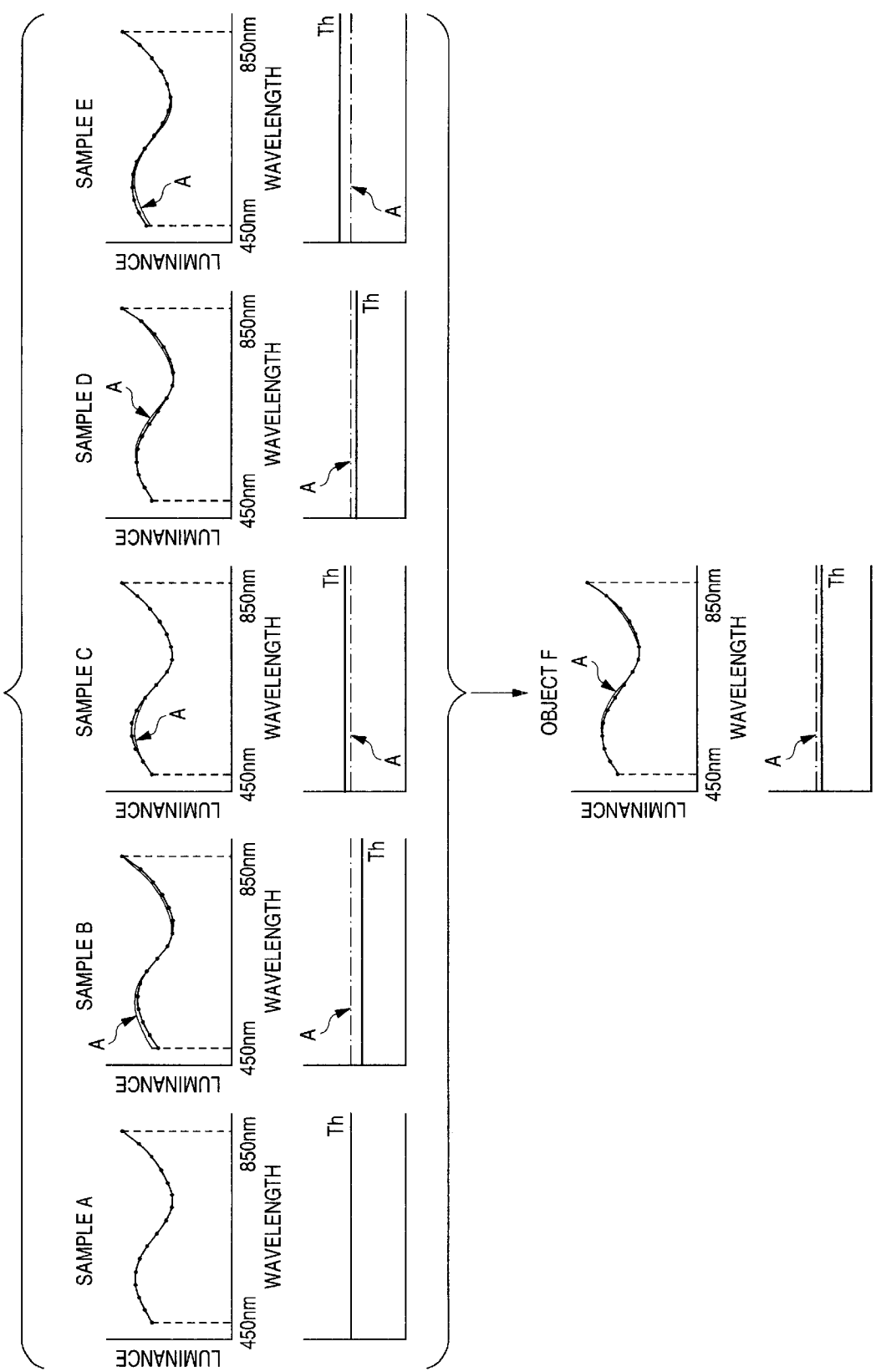
FIG. 5 is an explanatory drawing for explaining the output of an optimum inspection condition of a new wafer.

FIG. 5 is an explanatory drawing for explaining the output of an optimum inspection condition (a threshold level (Th) in FIG. 5) of a new wafer. The wavelength characteristic and the threshold level of a sample wafer A are shown in each wavelength characteristic (each luminance information) and each threshold level of sample wafers B to E and a wafer F which is an object of inspection, respectively in FIG. 5, so that difference is apparent. When the wavelength characteristic of the wafer F is input to the neural network 22, the threshold level of the wafer F is determined and output based upon relationship between each wavelength characteristic and each threshold level of the already learned (stored) wafers A to E (actually, more sample wafers are learned (stored), however, in FIG. 5, the case of five sample wafers is shown)

Relationship between the determined inspection condition and the corresponding wavelength characteristic is further learned and stored by the neural network 22.

Next, an example of defect detection by the detector 20c will be described. In the example, a defect is detected by regular reflection by bright field illumination. The rotary plate 5 of the illumination unit 2 is rotated under the control of the controller 30 and the opening of the rotary plate 5 is located on the path of illumination light. Hereby, the wafer W put on the stage 32 is illuminated by illumination light diffused via a diffusion plate 7. The image of the wafer W is imaged by regular reflection from the wafer W owing to the illumination by the camera 11. Image data from the camera 11 is fetched and stored in the memory 20a of the image processor 20.

A defect detection is performed by differentially processing a reference image which is of an indefective wafer and is previously stored in the memory 20a and the image of the newly stored wafer W which is an object of inspection. The inspection condition output from the neural network 22 is applied to the defect detection. That is, the parameter of the filtering processing is applied to the image processing and the threshold level for the binarizing processing is applied to the defect detection (judging whether a defect exists or not). When the differential image has a larger value than the threshold level, the detector 20c judges that the defect exists, and the result of the judgment is displayed on a monitor 24. In case a specific wavelength is an inspection condition, the wavelength of illumination light when the image of the wafer W is fetched is set by the filter 4.

In case the wafer W which is an object of inspection has a cyclic pattern, a defect can be also inspected by comparing (differentially processing) adjacent patterns in one image data. Further, two image data are acquired by displacing the wafer W so that positional relationship between the camera 11 and a pixel/the cyclic pattern is equal, and then a defect maybe also inspected by comparing (differentially processing) the two image data (refer to EPO930498 (N8C-111799 by these inventors). In case the wafer W has a cyclic pattern, moiré is formed due to relationship between the pixel cycle of the camera 11 and the cycle of the pattern on the wafer W, however, defect inspection with eliminating the effect of a pseudodefect which the moiré has can be executed by this method.

The manufacturing process of a semiconductor wafer includes many steps and an inspection condition for defect inspection greatly differs every step. Therefore, if the neural network 22 every step is prepared, a large quantity of learning is not required and the output of a more precise inspection condition is enabled.

In the above-mentioned embodiment, to obtain a wavelength characteristic, light is varied so that the light has 16 types of wavelengths, however, if light is varied so that the light has at least two types of wavelengths, a characteristic for the variation of the wavelengths (a characteristic of the variation of luminance information) can be extracted.

As described above, according to the invention, labor for setting the inspection condition of an unknown object is greatly reduced, the unknown object can be efficiently inspected and further, defect inspection can be also automated.

What is claimed is:

1. A defect inspection method of macroscopically inspecting a presence of a defect on an object, the defect inspection method comprising the steps of:

obtaining a plurality of images by serially illuminating a plurality of samples with a plurality of narrow-band light whose centers of wavelengths differ from each other, wherein inspection conditions for each of the plurality of samples are previously determined;

inputting wavelength characteristics of each of the plurality of samples obtained from luminance information of each image with respect to each center of wavelength to a neural network;

inputting the inspection conditions suitable for each of the samples as a teaching signal;

learning and storing the inputted wavelength characteristic of each sample and the inputted inspection condition for each sample correspondingly;

obtaining a plurality of images by serially illuminating an object, whose inspection condition is not determined, with the plurality of narrow-band light whose centers of wavelength differ from each other;

inputting a wavelength characteristic of the object obtained from luminance information of each image with respect to each center of wavelength to the neural network;

determining an inspection condition for the object based on the inputted wavelength characteristic of the object and the wavelength characteristic of each sample and the inspection condition for each sample which has been learned and stored; and outputting the determined inspection condition for the object.

2. The defect inspection method according to claim 1 further comprising the step of:

learning and storing the inputted wavelength characteristic of the object and the determined inspection condition for the object correspondingly.

3. The defect inspection method according to claim 1, wherein in the learning and storing step, the wavelength characteristic of the following sample and the inspection condition for the following sample are correspondingly learned and stored referring to the relationship between the wavelength characteristic of the previous sample and the inspection condition for the previous sample.

4. The defect inspection method according to claim 1, further comprising the steps of:

executing differential processing between a reference image and the image of the object for obtaining a differential image;

binarizing the differential image for obtaining a binarization data; and detecting the defect based on the binarization data.

5. The defect inspection method according to claim 4, wherein the inspection condition includes a threshold level referred in the binarizing step.

6. The defect inspection method according to claim 4, further comprising:

a step of filtering the differential image, the inspection condition includes a parameter for the filtering.

7. A defect inspection apparatus for macroscopically inspecting a presence of a defect on an object, the defect inspection apparatus comprising:

a first image obtaining unit for obtaining a plurality of images by serially illuminating a plurality of samples with a plurality of narrow-band light whose centers of wavelengths differ from each other, wherein inspection conditions for each of the plurality of samples are previously determined;

a neural network;

a first input unit which inputs wavelength characteristics of each of the plurality of samples obtained from luminance information of each image with respect to each center of wavelength to the neural network;

a second input unit which inputs the inspection conditions suitable for each of the samples as a teaching signal;

a second image obtaining unit for obtaining a plurality of images by serially illuminating an object, whose inspection condition is not determined, with the plurality of narrow-band light whose centers of wavelength differ from each other;

a third input unit which inputs a wavelength characteristic of the object obtained form luminance information of each image with respect to each center of wavelength to the neural network;

wherein the neural network correspondingly learns and stores the inputted wavelength characteristic of each sample and the inputted inspection condition for each sample, determines an inspection condition for the object based on the inputted wavelength characteristic of the object and the wavelength characteristic of each sample and the inspection condition for each sample which has been learned and stored, and outputs the determined inspection condition of the object.

8. The defect inspection apparatus according to claim 7, wherein the neural network further learns and stores the inputted wavelength characteristic of the object and the determined inspection condition for the object correspondingly.

9. The defect inspection apparatus according to claim 7, wherein the neural network learns and stores the wavelength characteristic of the following sample and the inspection condition for the following sample correspondingly referring to the relationship between the wavelength characteristic of the previous sample and the inspection condition for the previous sample.

10. The defect inspection apparatus according to claim 7, further comprising defect detecting means for executing differential processing between a reference image and the image of the object for obtaining a differential image, for binarizing the differential image for obtaining a binarization data, and for detecting the defect based on the binarization data.

11. The defect inspection apparatus according to claim 10, wherein the inspection condition includes a threshold level referred for binarizing.

12. The defect inspection apparatus according to claim 10, wherein the defect detecting means filters the differential image, the inspection condition includes a parameter for filtering.

* * * * *